(12) United States Patent　　(10) Patent No.: US 8,615,404 B2
Karkanias et al.　　(45) Date of Patent: Dec. 24, 2013

(54) SELF-DESCRIBING DATA FRAMEWORK

(75) Inventors: Chris Demetrios Karkanias, Sammamish, WA (US); Stephen Edward Hodges, Cambridge (GB)

(73) Assignee: Microsoft Corporation, Redmond, WA (US)

( * ) Notice: Subject to any disclaimer, the term of this patent is extended or adjusted under 35 U.S.C. 154(b) by 1253 days.

(21) Appl. No.: 11/678,266

(22) Filed: Feb. 23, 2007

(65) Prior Publication Data

US 2008/0208621 A1　Aug. 28, 2008

(51) Int. Cl.
*G06Q 50/00*　　(2012.01)
*G06F 15/18*　　(2006.01)

(52) U.S. Cl.
USPC .............................................. 705/2; 706/12

(58) Field of Classification Search
USPC ........................................................ 705/2–4
See application file for complete search history.

(56) References Cited

U.S. PATENT DOCUMENTS

| | | | |
|---|---|---|---|
| 6,611,846 B1 | 8/2003 | Stoodley | |
| 6,792,577 B1 | 9/2004 | Kimoto | |
| 7,082,441 B1 | 7/2006 | Zahavi et al. | |
| 7,158,990 B1 | 1/2007 | Guo et al. | |
| 7,983,933 B2 | 7/2011 | Karkanias et al. | |
| 8,005,692 B2 | 8/2011 | Karkanias et al. | |
| 8,065,161 B2 * | 11/2011 | Howard et al. ................... | 705/2 |
| 2001/0032099 A1 * | 10/2001 | Joao ................................. | 705/2 |
| 2002/0109600 A1 | 8/2002 | Mault et al. | |
| 2003/0084035 A1 | 5/2003 | Emerick, III | |
| 2003/0187615 A1 | 10/2003 | Epler et al. | |
| 2004/0225200 A1 | 11/2004 | Edmundson et al. | |
| 2005/0066190 A1 | 3/2005 | Martin | |
| 2005/0071624 A1 * | 3/2005 | Rothman et al. ............... | 713/100 |
| 2005/0132070 A1 | 6/2005 | Redlich et al. | |
| 2005/0177725 A1 * | 8/2005 | Lowe et al. .................... | 713/176 |
| 2006/0041570 A1 | 2/2006 | Lowe et al. | |
| 2006/0085422 A1 | 4/2006 | Moyaux et al. | |
| 2006/0112104 A1 | 5/2006 | An et al. | |
| 2006/0235811 A1 | 10/2006 | Fairweather | |
| 2006/0242097 A1 | 10/2006 | Gu et al. | |

(Continued)

FOREIGN PATENT DOCUMENTS

| | | |
|---|---|---|
| KR | 101998025157 | 7/1998 |
| KR | 1020020075846 | 10/2002 |
| KR | 1020060054977 | 5/2006 |

OTHER PUBLICATIONS

International Search Report for PCT Patent Application No. PCT/US2008/054812, dated Jul. 31, 2008, 10 pages.

(Continued)

*Primary Examiner* — Luke Gilligan
*Assistant Examiner* — Kristine Rapillo

(57) ABSTRACT

A system that can enable establishment of a self-describing data network is provided. Generally, the innovation provides a mechanism by which self-describing data can be collected, validated and stored in such a way that permits each data element to be inherently self-describing. The manner in which the data is stored can be analogized to a 'data chemistry' whereby data is stored in the smallest meaningful bit (e.g., atom) coupled with descriptive metadata (e.g., tags). In a specific example, the data network maintains health-related data where each element includes a core data element wrapped with descriptive metadata. The descriptive metadata (e.g., tags) can be employed to interrelate the data elements for storage as well as to facilitate efficient traversal of the data network as a whole.

20 Claims, 12 Drawing Sheets

(56) References Cited

U.S. PATENT DOCUMENTS

| | | | |
|---|---|---|---|
| 2007/0106537 A1* | 5/2007 | Moore | 705/3 |
| 2007/0260492 A1 | 11/2007 | Feied et al. | |
| 2008/0082356 A1* | 4/2008 | Friedlander et al. | 705/2 |
| 2008/0138783 A1 | 6/2008 | Karkanias et al. | |
| 2008/0183049 A1 | 7/2008 | Karkanias et al. | |

OTHER PUBLICATIONS

International Search Report and Written Opinion for Application No. PCT/US2008/054810 dated Jul. 25, 2008.

Chilean OA, mailed Jun. 3, 2011, for Chilean Patent Application No. 533-2008, 5 pages (untranslated).

Meg Murray. An Investigation of Specifications for Migrating to a Web Portal Framework for the Dissemination of Health Information within a Public Health Network. http://csdl2.computer.org/comp/proceedings/hicss/2002/1435/06/14350145.pdf. Last accessed Nov. 21, 2006.

Robert G. Cromley, et al. Integrating Spatial Metadata and Data Dissemination Over the Internet. http://iassistdata.org/publications/iq/iq26/iqvol261cromley.pdf. pp. 13-16. Last accessed Nov. 21, 2006.

Laser Interferometer Gravitational Wave Observatory. California Institute of Technology and Massachusetts Institute of Technology. http://www.ligo.caltech.edu/docs/T/T980070-02.pdf. Last accessed Nov. 21, 2006.

Office Action from the Taiwan Intellectual Property Office for Application No. 97106364 dated Oct. 15, 2013, 12 pages.

* cited by examiner

SELF-DESCRIBING DATA FRAMEWORK

BACKGROUND

Computers and computer related technology have evolved significantly over the past several decades to the point where vast amounts of computer readable data is being created and stored daily. Most often, this data is being stored locally within conventional relational databases. Digital computers were initially simply very large calculators designed to aid performance of scientific calculations. Only many years later had computers evolved to a point where they were able to execute stored programs. Subsequent rapid emergence of computing power produced personal computers that were able to facilitate document production and printing, bookkeeping as well as business forecasting, among other things. Constant improvement of processing power coupled with significant advances in computer memory and/or storage devices (as well as expediential reduction in cost) have led to persistence and processing of an enormous volume of data, which continues today. For example, data warehouses are now widespread technologies employed to support business decisions over terabytes of data.

Unfortunately, today, data warehouses are maintained separately within relational databases and are most often directed to application specific environments controlled by a variety of application service providers. A relational database refers to a data storage mechanism that employs a relational model in order to interrelate data. These relationships are defined by a set of tuples that all have a common attribute. The tuples are most often represented in a two-dimensional table, or group of tables, organized in rows and columns.

The sheer volume of collected data in databases (e.g., relational databases) made it nearly impossible for a human being alone to perform any meaningful analysis, as was done in the past. This predicament led to the development of data mining and associated tools. Data mining relates to a process of exploring large quantities of data in order to discover meaningful information about the data that is generally in the form of relationships, patterns and rules. In this process, various forms of analysis can be employed to discern such patterns and rules in historical data for a given application or business scenario. Such information can then be stored as an abstract mathematical model of the historical data, referred to as a data-mining model (DMM). After the DMM is created, new data can be examined with respect to the model to determine if the data fits a desired pattern or rule.

Unfortunately, data mining is employed upon data stored within relational databases in a closed environment, frequently by large corporations, for example, to understand complex business processes. This can be achieved through discovery of relationships or patterns in data relating to past behavior of a business process. Such patterns can be utilized to improve the performance of a process by exploiting favorable and avoiding problematic patterns.

SUMMARY

The following presents a simplified summary of the innovation in order to provide a basic understanding of some aspects of the innovation. This summary is not an extensive overview of the innovation. It is not intended to identify key/critical elements of the innovation or to delineate the scope of the innovation. Its sole purpose is to present some concepts of the innovation in a simplified form as a prelude to the more detailed description that is presented later.

The innovation disclosed and claimed herein, in one aspect thereof, comprises a system that can enable establishment of a self-describing data network. In a specific example, the data network maintains health-related data where each element includes a core data element wrapped with descriptive metadata. The descriptive metadata (e.g., tags) can be employed to interrelate the data elements as well as to facilitate efficient traversal of the data network as a whole. Essentially, the innovation provides a mechanism by which data can be collected, validated and stored in such a way that permits each data element to be inherently self-describing. This self-describing property can enhance and optimize usability of the data network in accordance with operations such as data mining, querying, etc.

In accordance with the innovation, health-related data can be drilled down into the smallest meaningful component and subsequently surrounded with metadata that describes the nature of the data as well as how to interact with the data. This data arrangement can enable information to emerge out of a suitably organized data set. This data set can be viewed as 'simultaneously relational' because the metadata enables relationships to be established just-in-time as needed and/or desired. Moreover, this data set can leverage the power of a network of data by establishing relationships on-the-fly. The self-describing data elements of the innovation can be maintained within a pool, or 'soup', of data that can be organized in such a way that arbitrary paths can be established just-in-time.

In operation, the subject innovation enables organization of the captured data such that a user can traverse large areas of the data set without having a predetermined data model. In other words, to do so, the data model can be established just-in-time. In operation, metadata tagged to captured data can allow all data to exist in, and to be extracted as needed/desired from, a single pool. With reference to the principle of metadata driving the just-in-time pattern assembly in combination with mathematical principles, is can be possible to traverse a network of an arbitrarily large size in a finite number of steps. This is particularly useful as relationships between information in the pool can be established just-in-time in only a few operations despite its vast size.

The same dynamics are applicable in a graph theory spirit. For example, the Hilbert space allows for mathematical treatment of operating on multi-dimensional data sets in arbitrary space. Thus, rather than looking at graphs in the typical two or three dimensional scenario, the innovation enables data to be manipulated in large (e.g., 50, 100, 1000) dimensional graphs. It will be understood that the vector within the space is finite regardless of the number of dimensions employed. Although an infinite number of points will most likely not be available within the pool, one feature of the innovation is that operations can be performed upon the data in order to establish relationships just-in-time regardless of the number of data points. The mere storage of the data in this graph space is also the query. Thus, in effect, storage of the data produces the result.

To the accomplishment of the foregoing and related ends, certain illustrative aspects of the innovation are described herein in connection with the following description and the annexed drawings. These aspects are indicative, however, of but a few of the various ways in which the principles of the innovation can be employed and the subject innovation is intended to include all such aspects and their equivalents. Other advantages and novel features of the innovation will become apparent from the following detailed description of the innovation when considered in conjunction with the drawings.

DETAILED DESCRIPTION

Figure 1:
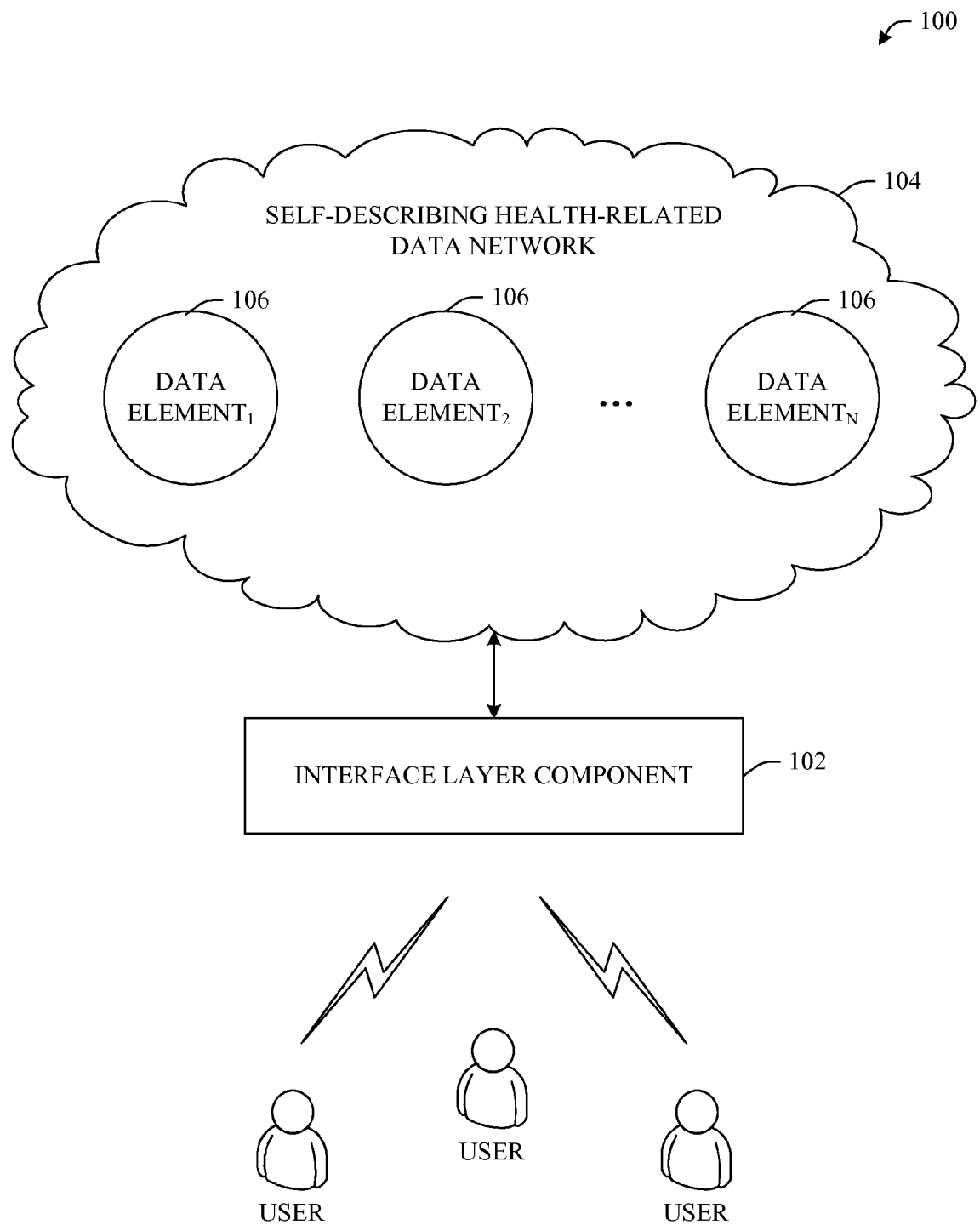
FIG. 1 illustrates a system that establishes a self-describing health-related data network in accordance with an aspect of the innovation.

The innovation is now described with reference to the drawings, wherein like reference numerals are used to refer to like elements throughout. In the following description, for purposes of explanation, numerous specific details are set forth in order to provide a thorough understanding of the subject innovation. It may be evident, however, that the innovation can be practiced without these specific details. In other instances, well-known structures and devices are shown in block diagram form in order to facilitate describing the innovation.

As used in this application, the terms "component" and "system" are intended to refer to a computer-related entity, either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution, and a component can be localized on one computer and/or distributed between two or more computers.

As used herein, the term to "infer" or "inference" refer generally to the process of reasoning about or inferring states of the system, environment, and/or user from a set of observations as captured via events and/or data. Inference can be employed to identify a specific context or action, or can generate a probability distribution over states, for example. The inference can be probabilistic—that is, the computation of a probability distribution over states of interest based on a consideration of data and events. Inference can also refer to techniques employed for composing higher-level events from a set of events and/or data. Such inference results in the construction of new events or actions from a set of observed events and/or stored event data, whether or not the events are correlated in close temporal proximity, and whether the events and data come from one or several event and data sources.

Referring initially to the drawings, FIG. 1 illustrates a system 100 that enables data to be self-describing such that the data need not be stored within a specified pre-defined structure (e.g., relational database). However, it is to be understood and appreciated that, although data is discussed as being stored within the smallest possible unit, it is to be understood that other aspects exist where data is stored within conventional databases or a combination of conventional databases together with atomized elements. These alternative aspects will be better understood upon a review of the figures that follow.

Generally, system 100 includes an interface layer 102 that provides a gateway between a source or origin of data and a self-describing health-related data network 104, hereinafter referred to as data network 104. As illustrated, the data network 104 can include 1 to N data elements 106, where N is an integer. Effectively, it is to be understood that, unlike limitations imposed upon conventional two-dimensional relational tables, data network 104 can be N-dimensional in structure whereby the structure can constantly change in accordance with stored data.

Generally, system 100 can provide ways to capture and leverage information in the health care and education spaces. For example, many of the ideas presented facilitate ways to improve health diagnosis and treatment as well as to assist in the promotion of healthy living. Additionally, it will become apparent to those skilled in the art that these ideas suggest many monetization techniques that leverage the 'soup' of captured information (e.g., data network 104).

Although the aspects described herein are specifically directed to health-related data, alternate aspects of the features, functions and/or benefits of the innovation can be directed to other industry-specific data. By way of example and not limitation, the concepts described herein can be directed to financial information, automobile information, product satisfaction information, media broadcast information, or the like. Thus, alternative aspects which can employ the data collection, validation and sharing concepts described herein are to be considered within the scope of this disclosure and claims appended hereto.

Continuing with the health-related aspects, two major pillars of incubation in the space of health strategies are health and education. These pillars are interrelated segments of a framework that identifies a comprehensive solution set that can be released into the market globally. Because health behavior modification is oftentimes education based, the interrelated nature of these pillars can be easily understood.

Consumer orientation is an important aspect to a solution in this area. Thus, there is great value in having an integrated data platform with services and attributes wrapping data in a service-orientated manner. In one aspect, these services can provide means to enable users to navigate through the health and wellness states. The system 100 can address enablement of an appropriate data platform to create a paradigm shift that makes the health care system compete on value as opposed to competing on cost. Rather than operationalizing down how to deliver the minimum product for the minimum price, the innovations described herein address how to deliver maximum value where scale of the data platform (e.g., data network 104) provides for economic reduction of cost. Effectively, integrated data can provide for activating changes in behaviors of persons—awareness is half of the battle. In doing so, the subject innovation addresses aspects of the information supply chain that include collection, validation, and storage of self-describing data elements 106.

Figure 2:
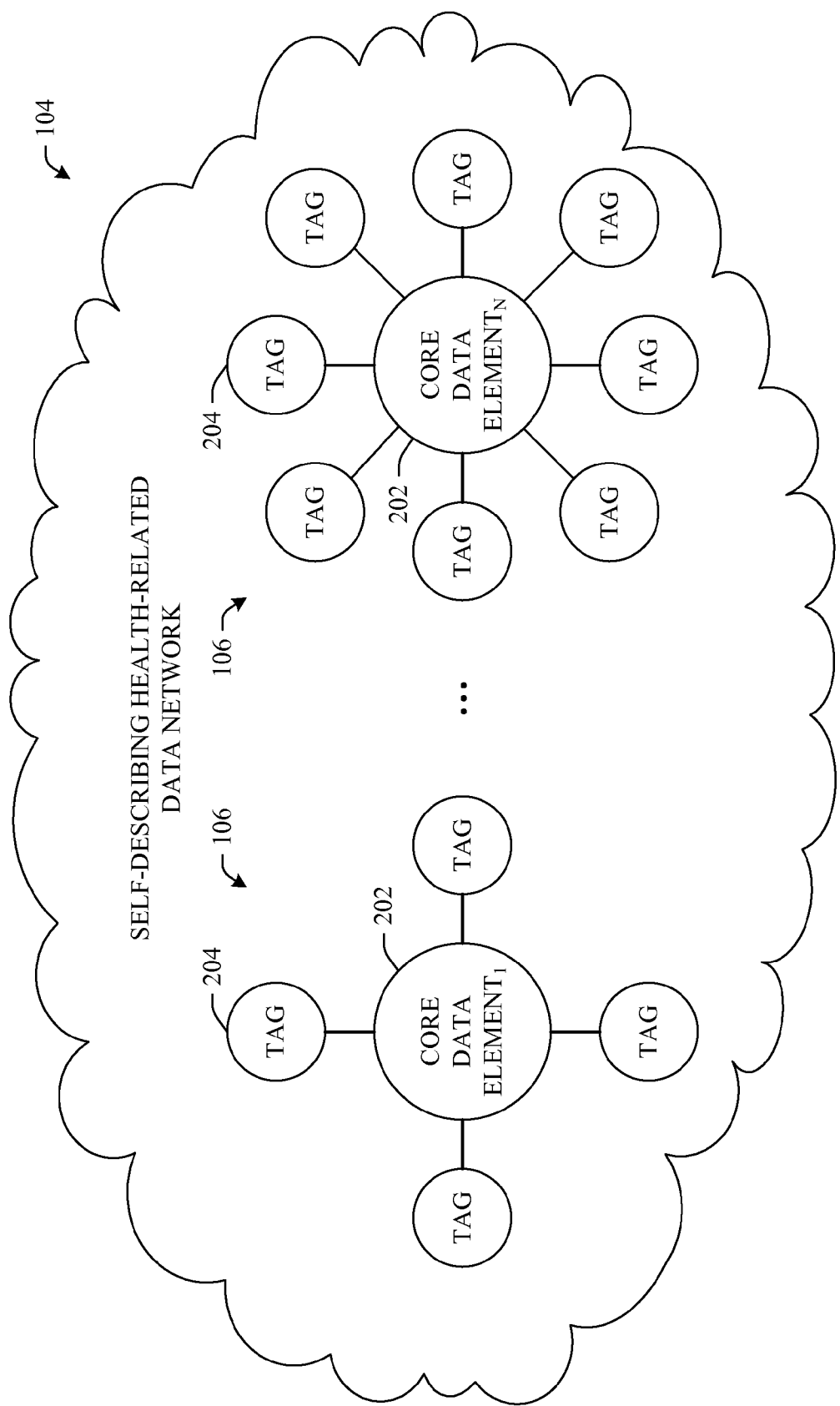
FIG. 2 illustrates an example self-describing health-care data network having N dimensions in accordance with an aspect of the innovation.

More particularly, the self-describing data elements 106 can be structured in such a way that they are wrapped (or tagged) with metadata that defines detailed attributes about the core data item. This concept can be better understood as illustrated in FIG. 2. As shown, each data element 106 within the data network 104 can include a core data element 202 and one or more attributes or descriptive data elements 204 (e.g., tag(s)). As described above, the conventional canonical way of working with data was to develop a model or defined structure/framework thereafter collecting and storing data in accordance with the predefined model, structure or framework. This conventional method of organizing data can limit use as conventional categories had to be predetermined in order to know what to collect and where to store what has been collected.

Contrary to conventional approaches, the subject specification discloses a 'self-describing' data network 104 where each of the data elements 106 include information (e.g., tags 204) that inherently describes the nature, origin, substance, context, relationship, etc. of the core data element 202. In this manner, the information mechanics of the data network 104 enable relationships to be made on-the-fly or just-in-time dynamically without the need for any predefined model. As such, data networks (e.g., data network 104) having a vast number of data elements (e.g., millions, billions) can be traversed with a limited number of hops (e.g., 10) in order establish and subsequently leverage interconnectivity between the elements.

In one aspect, known principles and algorithmic techniques such as 'Small World' theorem or analysis can be employed to illustrate the ability to traverse such a vast amount of data in such a limited number of hops. Effectively, Small World concepts teach that, from statistical physics, a large class of complex networks characterized by high clustering properties includes amazingly short paths between pairs of nodes (e.g., data elements 106). Further, this ability to traverse a complex network can also be explained analogously with the concept of 'Six Degrees of Separation.' This concept has been demonstrated in areas ranging from acquaintances between individuals in the United States, to telephone call graphs, to data packet (e.g., email) delivery via the worldwide web (e.g., Internet).

Another analogy of the overall concept of the innovation is that of chemistry. In other words, the data network 104 of FIG. 2 illustrates data elements 106 that resemble atoms as used in chemistry. Accordingly, in aspects, the core data element 202 can be representative of a smallest sensible bit of information imaginable that is wrapped with metadata (e.g., tags 204) that describe the atomized bit. The described structure of the data elements 106 enables just-in-time combination and/or re-combination to essentially form data models.

The following example is included to provide perspective to the innovation and is not intended to limit the scope of the innovation in any way. Suppose that the data element 106 is representative of John Doe's blood pressure measurement. Here, the core data element 202 can be representative of a systolic pressure measurement which represents the maximum pressure in an artery at the moment when the heart is beating and pumping blood through the body. Similarly, another core data element 202 can be representative of a corresponding diastolic pressure measurement which is the lowest pressure in an artery in the moments between beats when the heart is resting.

Essentially, these core data elements 202 can be merely a numerical value where descriptive attributes, e.g., tags 204, can be associated to describe and interrelate the data. Continuing with this example, a tag can be attached that defines meaning of the value (e.g., blood pressure measurement), for example, the units of measurement for the numerical value (e.g., millimeters of mercury (mmHg)), the source/origin of the measurement, the method of reading, time/date of reading, patient context when reading was taken, relationships to other blood pressure measurements as well as other medical records, how to interact with the measurement, interesting issues relating to the measurement, etc. It will be understood that the granularity of the tags can be a function of most any criteria including, but not limited to, user preference, industry standards, corporate regulations, governmental regulations, inference, etc.

Once the measurement is stored within the self-describing network 104, it becomes possible to pivot the network 104 upon this blood pressure measurement as well as measurements in general. As will be understood, pivots can also be constructed upon information stored as attributes (e.g., tags 204) relating to core data items 202. A simplified example of traversal could hop from John Doe's blood pressure measurement, to patient Jim, to nurse Jane, to other blood pressure measurements administered by nurse Jane.

As described supra, this traversal can be analogized to TCP/IP (transmission control protocol/Internet protocol) which is a routable communications protocol for the Internet. In accordance with this protocol, data packets can arrive, intact and complete at a final target destination by only knowing the next hop at any one time. In operation, packet headers include source and destination information such that a packet can traverse the Internet subsequently arriving at a desired target location. Here, the tags 204 can include this information in a suitably standard format that defines how metadata is collected and wrapped to core data elements 202.

The health-related data network 104 can be structured in such a way that it is effectively an N-dimensional data structure, where N is an integer. In other words, vectors can be drawn between data elements having the same or similar characteristics (e.g., tags 202) such that interconnectivity can easily be identified to facilitate pattern and trend identification for the purposes of health-related matters. Moreover, the N-dimensional health-related data network 104 can enable the data to be analyzed and/or shared thereby establishing an efficient and intelligent system of data sharing as applied to health-related matters. It is to be understood and appreciated that, in aspects, the system 100 of FIG. 1 essentially enables a third party (or group of third parties) to maintain health-related data which can be easily shared and intelligently mined to assess health-related topics.

Figure 3:
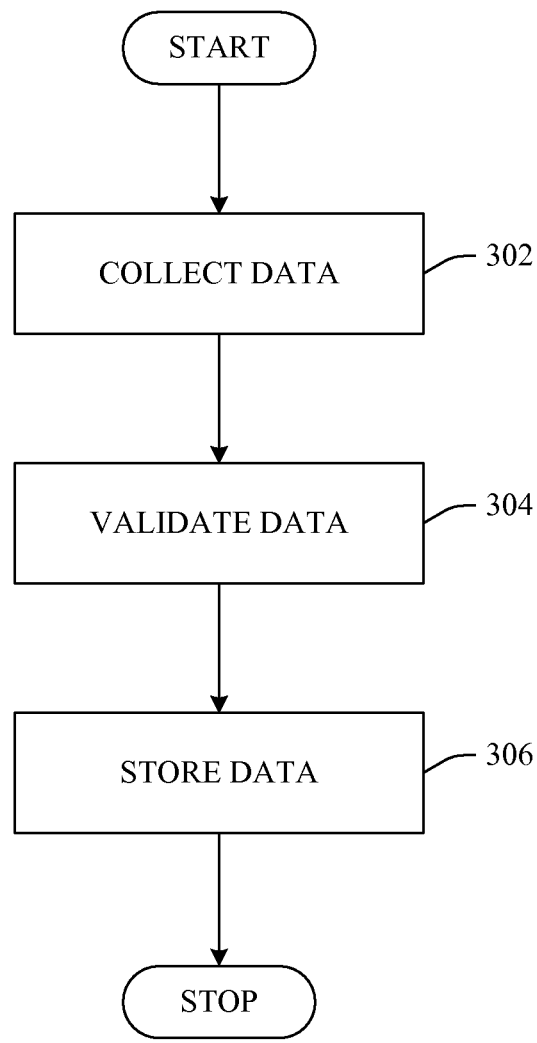
FIG. 3 illustrates an exemplary flow chart of procedures that facilitate collection, validation and storage of health-related data in accordance with an aspect of the innovation.

FIG. 3 illustrates a methodology of managing health-related data in accordance with an aspect of the innovation. While, for purposes of simplicity of explanation, the one or more methodologies shown herein, e.g., in the form of a flow chart, are shown and described as a series of acts, it is to be understood and appreciated that the subject innovation is not limited by the order of acts, as some acts may, in accordance with the innovation, occur in a different order and/or concurrently with other acts from that shown and described herein. For example, those skilled in the art will understand and appreciate that a methodology could alternatively be represented as a series of interrelated states or events, such as in a state diagram. Moreover, not all illustrated acts may be required to implement a methodology in accordance with the innovation.

At 302, data elements can be collected for example, health-related data elements 106 of FIG. 1 can be gathered. In operation, these data elements can be automatically and/or dynamically collected in most any manner ranging from push/pull from sensor technologies, applications, user-initiated actions or the like. In one example, image recorders, medical instruments, etc. can be equipped to automatically transmit data by way of an interface (e.g., 102 of FIG. 1).

Once collected, at 304, the data can be validated with regard to most any desired factor(s), for example, completeness, integrity, value, etc. Additionally, at 306, the data can be maintained within a storage mechanism for subsequent retrieval, access, processing or use. Although a specific ordering of acts is illustrated in FIG. 3, it is to be understood that, where possible, the acts can be enacted in alternative orders. For instance, data can be validated either before or after actual collection and/or storing. These alternative aspects are to be included within the scope of this disclosure and claims appended hereto.

Figure 4:
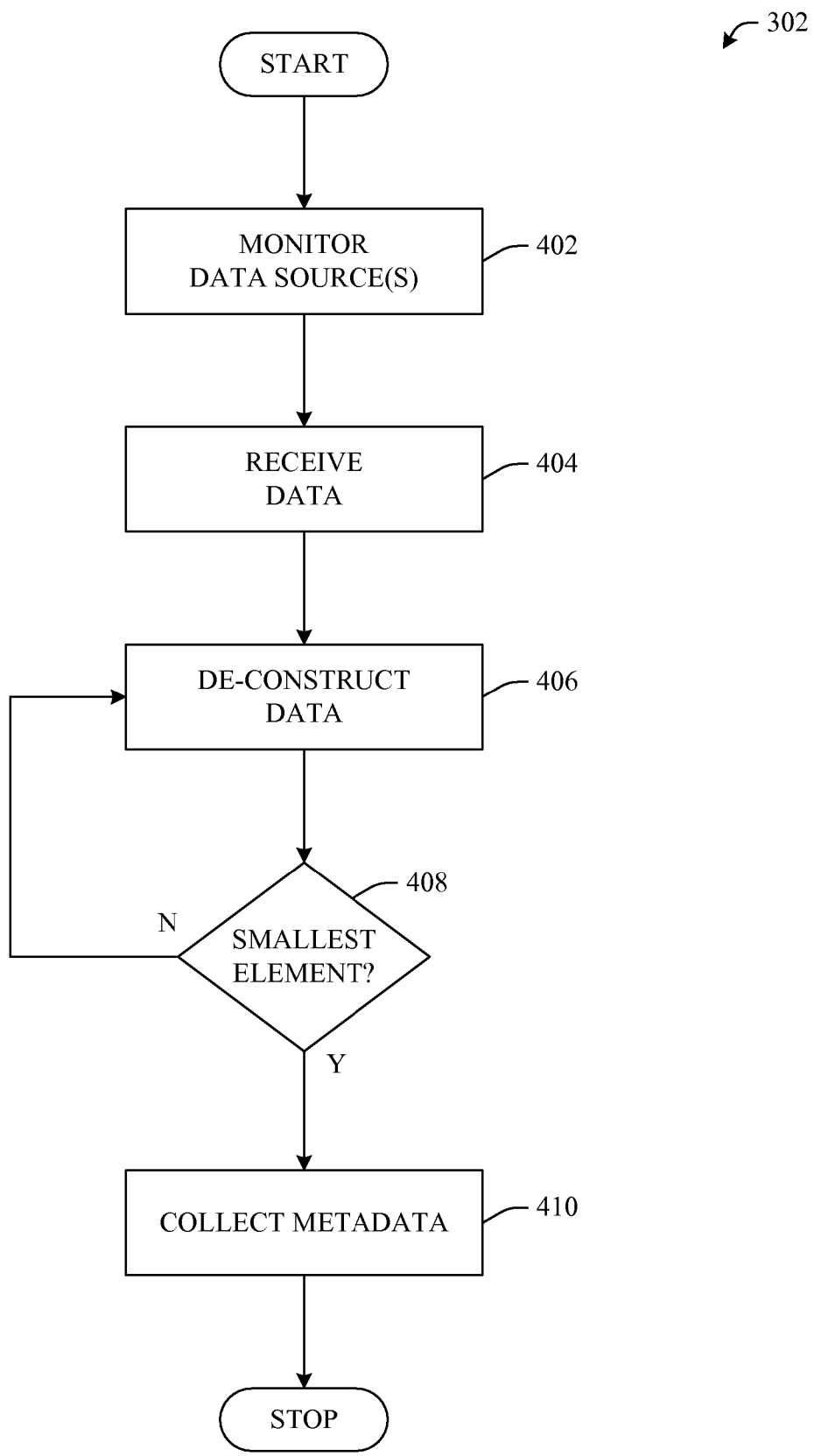
FIG. 4 illustrates an exemplary flow chart of procedures that facilitate data collection in accordance with an aspect of the innovation.

Referring now to FIG. 4, there is illustrated an example methodology of collecting data (e.g., act 302 of FIG. 3). At 402, a data source can be monitored, for example, physiological and/or environmental sensors can be actively monitored by which to capture data. Similarly, most any data source can be actively monitored to capture data, including but not limited to, financial trading markets, insurance markets, broadcast ratings, traffic patterns, etc. At 404, the data can be received by way of pushing and/or pulling the data from the source or origin.

The data can be de-constructed at 406 which effectively can separate the data element into the smallest sensible information bit (e.g., core data element 202 of FIG. 2). A determination is made at 408 to establish if the smallest sensible bit has been determined. If not, the data is further de-constructed at 406 as shown. If so, metadata that describes the smallest sensible bit (e.g., core data element 202 of FIG. 2) can be gathered. It is to be understood that this metadata can be gathered by way of the de-construction process at 406 or alternatively, by way of subsequent information gathering processes (e.g., 410).

Figure 5:
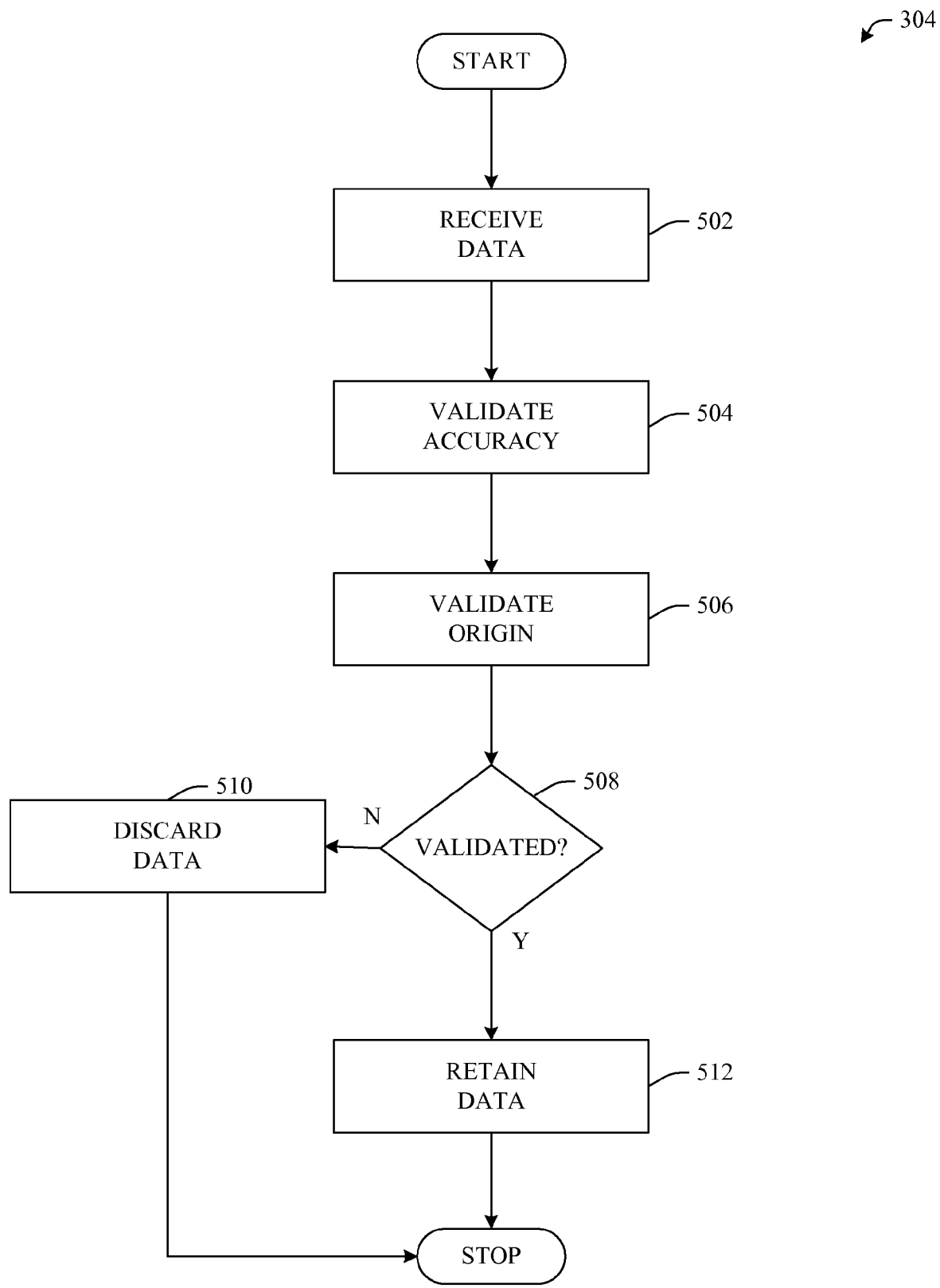
FIG. 5 illustrates an exemplary flow chart of procedures that facilitate data validation in accordance with an aspect of the innovation.

Referring now to FIG. 5, there is illustrated an example methodology of validating data (e.g., act 304 of FIG. 3). At 502, data is received, for example, data can be received in most any manner from most any source/origin. As described above, data can be pushed or pulled from a source in accordance with aspects of the innovation. Once received, at 504, accuracy of the data can be validated.

Continuing with the example above of capturing a blood pressure measurement, at 504, the accuracy can validated by employing a policy or threshold to compare the captured value to an industry standard range, historical patient data, statistical demographic values, etc. Essentially, accuracy confidence can be increased as a function of some predetermined or preprogrammed rules, inference, threshold or benchmark. In addition to the value itself, other factors can contribute to the validation process thereby increasing confidence levels. By way of example, experience of the health care professional, age of measuring device, similarity to previous measurements, etc. can all be considered to increase the validation confidence.

As the data is maintained in a cloud, 'soup' or pool of data, it is increasingly important to have safeguards in place to eliminate any malicious or accidental tainting of the integrity of the information in the network. While accuracy validation assists in this task, at 506, the origin of the data can also be validated in order to identify and/or discover any possibility of incorrect or contaminated data entering the network. This process can be analogized to spam filtering of emails. In one aspect, white and black lists can be managed in order to permit data to enter the network.

At 508, a determination is made if validation is successful. If not, at 510, the data is discarded and not retained for storage. On the other hand, if both the accuracy and origin are validated to a sufficient level of confidence, the data is retained at 512 for storage within the data network.

Figure 6:
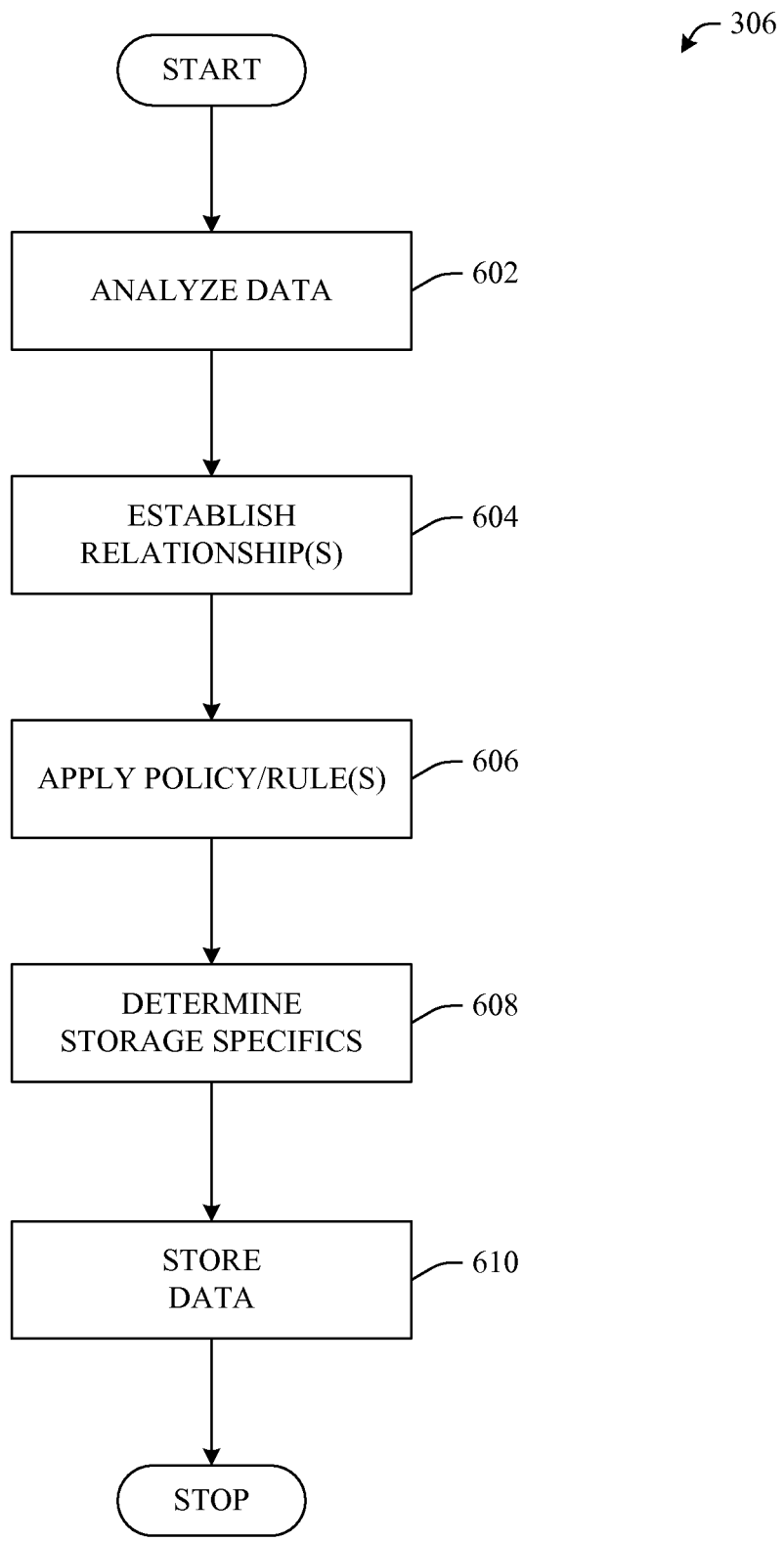
FIG. 6 illustrates an exemplary flow chart of procedures that facilitate data storage in accordance with an aspect of the innovation.

Referring now to FIG. 6, there is illustrated an example methodology of storing data (e.g., act 306 of FIG. 3). At 602, data elements can be analyzed. Accordingly, relationships of a subject data element to other data elements can be established at 604. In other words, implicit, previously unknown, and potentially useful information can be identified from the data element as a function of the data network. For example, at 606 a policy and/or rule can be applied in the analysis which can discern or recognize patterns and/or correlations amongst the stored health-related data to the subject data element. In doing so, a single or combination of analysis techniques can be employed including, without limitation, statistics, regression, neural networks, decision trees, Bayesian classifiers, Support Vector Machines, clusters, rule induction, nearest neighbor and the like to locate hidden knowledge within data. In one instance, a model can be built and trained in accordance with a type of data. Subsequently, the trained model can be employed to identify patterns and/or correlations of future elements of the same or similar type.

At 608, storage specifics are determined. For instance, optimal clustering techniques can be identified. As described supra, these clustering techniques can enhance the effectiveness of Small World analysis techniques of traversing the network. Once storage specifics are determined, at 610, the self-describing data can be stored within the self-describing data network.

Figure 7:
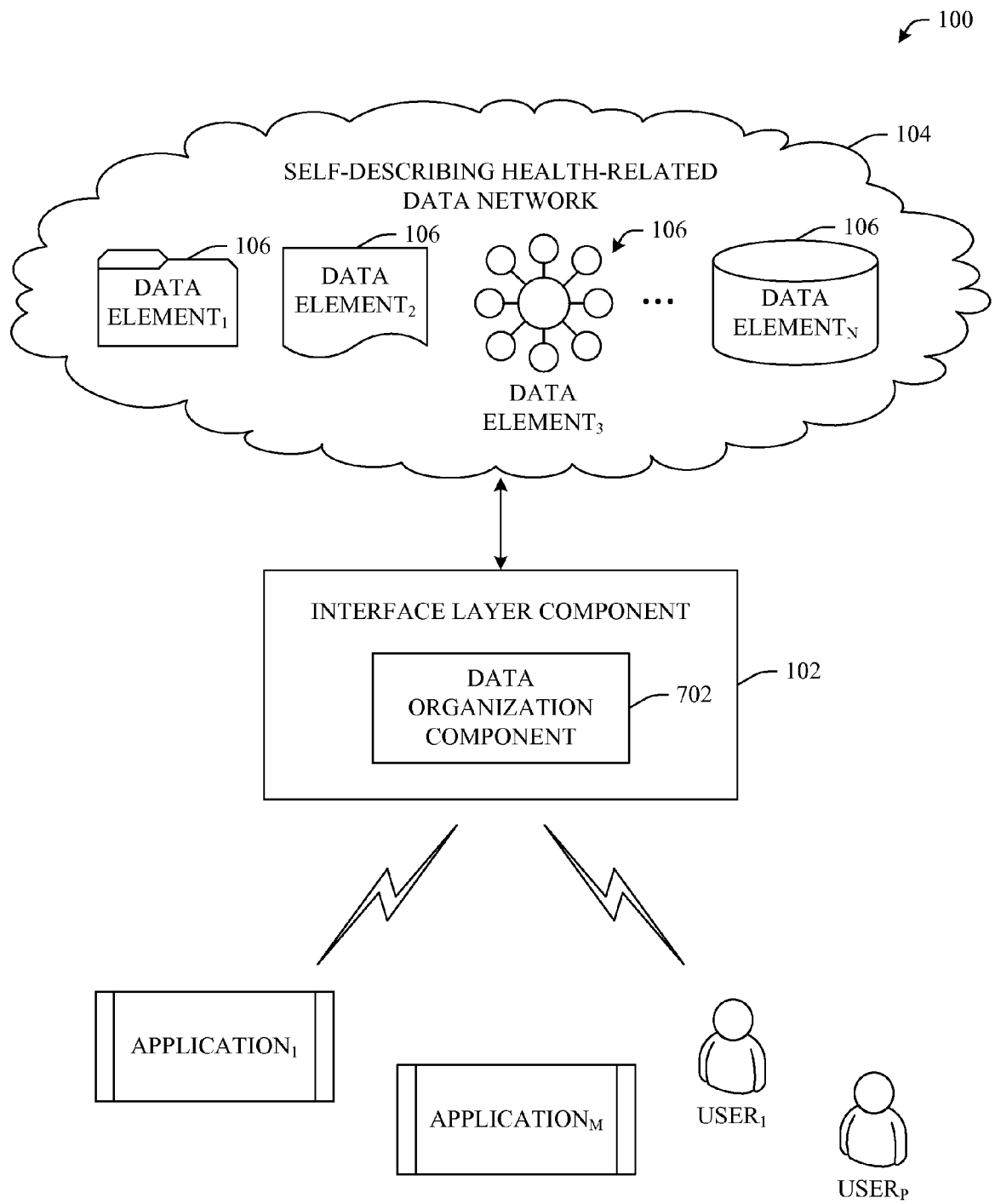
FIG. 7 illustrates an alternative block diagram of an example system that facilitates generation of a self-describing health-related data network.

FIG. 7 illustrates yet another alternative block diagram of system 100 in accordance with an aspect of the innovation. Specifically, FIG. 7 illustrates that data network 104 can include most any type of data elements 106 known in the art. For instance, as shown, data elements 106 can include, but are not limited to, conventional file folders that maintain documents and data, stand-alone documents, core data items tagged with metadata, disparate storage devices and/or relational database tables, as well as any combination thereof. Moreover, it is to be understood that, although data network 104 is illustrated as a single component, the network can be distributed within various clouds, enterprises, machines, etc. without departing from the spirit and/or scope of the innovation.

Additionally, FIG. 7 illustrates that data elements 106 can be obtained from most any source/origin including, but not limited to, 1 to M applications or 1 to P users where M and P are integers by way of a data organization component 702. For example, the users can be equipped with image recorder components (not shown) that can effectively capture a sequence of images that correspond to a user event. Additionally, other physiological and/or environmental sensory mechanisms can be employed that can dynamically push data to the network where it can be collected, validated and stored.

Figure 8:
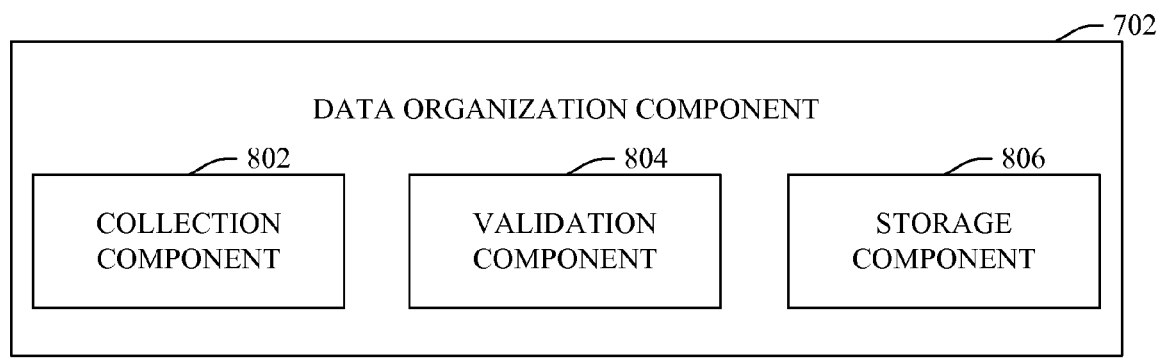
FIG. 8 illustrates an example data organization component that facilitates data collection, validation and storage in accordance with an aspect of the innovation.

FIG. 8 illustrates a block diagram of data organization component 702 in accordance with an aspect of the innovation. Generally, data organization component 702 can include a collection component 802, a validation component 804 and a storage component 806. Functionalities of each of these components have been described with reference to the figures above.

As previously described, the collection component 802 can facilitate either pulling or receiving pushed data from origins and/or sources. For example, the collection component 802 can automatically poll sensory mechanisms to populate the self-describing data network (e.g., 104 of FIG. 1). Continuing with the example from above, blood pressure readings can be automatically collected by the collection component 802 for storage within the data network.

The validation component 804 can facilitate at least two safeguards related to the integrity of the data network. First, the validation component 804 can validate the accuracy of the received data to detect any data issues related to the element in general as well as the transmission/reception of the data. Additionally, the validation component 804 can validate (e.g., authenticate) the source/origin of the data element. In this manner, the validated source/origin can be used to tag the core data element as described above as well as to potentially filter incoming data. For instance, white and/or black list filtering can be used to prohibit potentially bad actors from populating the data network.

The storage component 806 can facilitate data analysis that identifies relationships between a subject data element and those data elements maintained within the data network. This relationship data can be employed to facilitate clustering and/or logical/intelligent placement of data elements. It will be appreciated that proactive clustering can enhance usability of the data network when traversing to identify specific element types, patterns, trends, etc.

Figure 9:
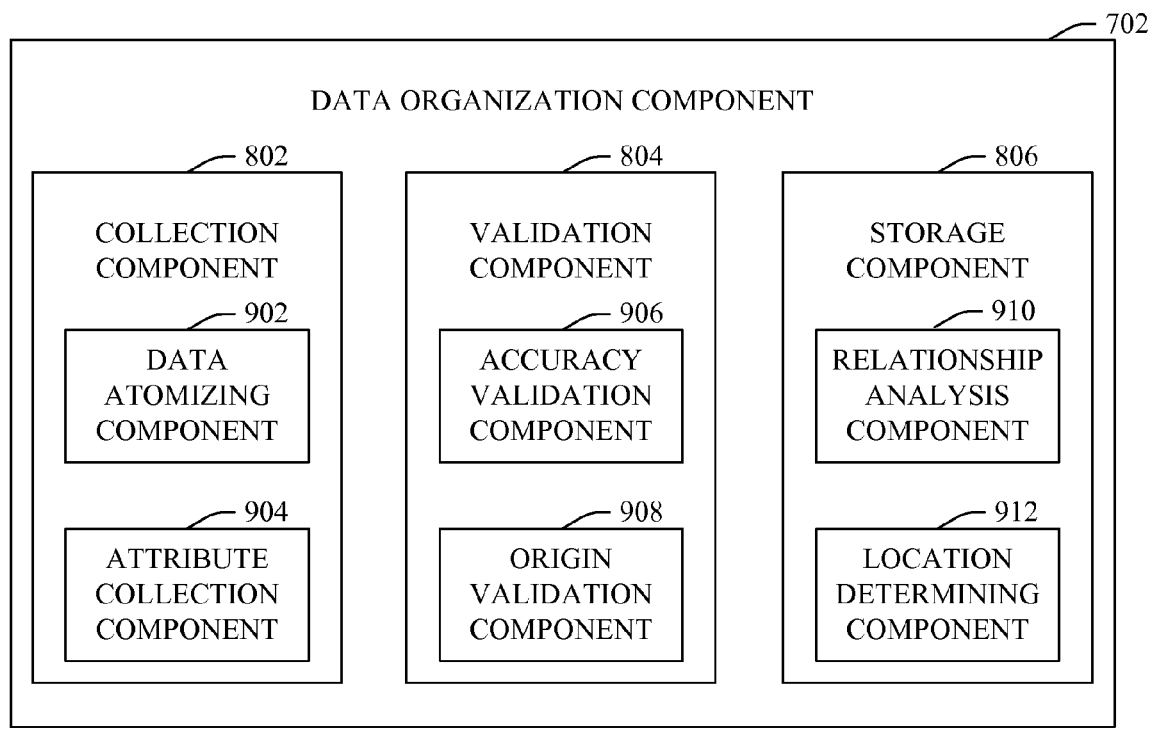
FIG. 9 illustrates a detailed block diagram of an example data organization component in accordance with an aspect of the innovation.

FIG. 9 illustrates a more detailed block diagram of an example data organization component 702 in accordance with an embodiment of the innovation. With reference first to the collection component 802, this component can include a data atomizing component 902 and an attribute collection component 904. The data atomizing component 902 can segregate received data elements into the smallest sensible bit of information together with any identifying or descriptive information. The attribute collection component 904 can further gather additional descriptive information which can be incorporated into the data element structure (e.g., core data element wrapped with descriptive metadata). Overall, the subcomponents (902, 904) of the collection component 802 facilitate generation of the self-describing data elements (e.g., 106 of FIG. 1).

As illustrated, the validation component 804 can include an accuracy validation component 906 and an origin validation component 908. Each of these components (906, 908) can be employed to minimize and/or eliminate the possibility of populating the data network with incorrect, useless or contaminated data. As described above, the accuracy validation component 906 can be employed to intelligently assess the received data element by determining what the data should be versus what it is. For example, if the data element represents a blood pressure measurement, it will be appreciated that this measurement has a defined range that corresponds to this type of measurement. As such, the accuracy validation component 906 can verify that the measurement falls within the range of values for this type of data.

The origin validation component 908 can further be used to self police the data that enters the data network. In doing so, the source and/or origin of each data element can be validated and if desired, subjected to a filtering mechanism (e.g., white/black list) that can effectively prohibit data from predefined sources. This white/black list technique is but one example of how the source/origin information can be employed to enhance the quality of data within the data network. Other examples include, tester/health care professional qualifications, age of testing equipment, location of origination, age of data, etc. Essentially, it is to be understood that most any desired criteria can be employed by the validation component 804 to control access to the data network.

Turning now to the storage component 806, this component can include a relationship analysis component 910 and a location determining component 912. Generally, these two subcomponents (910, 912) can facilitate intelligent clustering and/or placement of a data element within the data network. The relationship analysis component 910 can, based upon descriptive attributes and/or metadata, identify relationships (e.g., parallels, patterns, trends, etc.) between a subject element and other elements maintained within the data network. Accordingly, the location determining component 912 can employ this information to intelligently and/or logically cluster or place the data within the data network. Although it will be understood that this intelligent clustering and/or placement can facilitate efficient traversal of the data network, it is to be appreciated that the self-describing data network can be structured in an ad hoc manner. Whether constructed intelligently based upon relationships or structured in an ad hoc manner, the self-describing data network will, nonetheless, provide a framework which can be traversed in a fixed number of hops due to the descriptive attributes of each data element.

Figure 10:
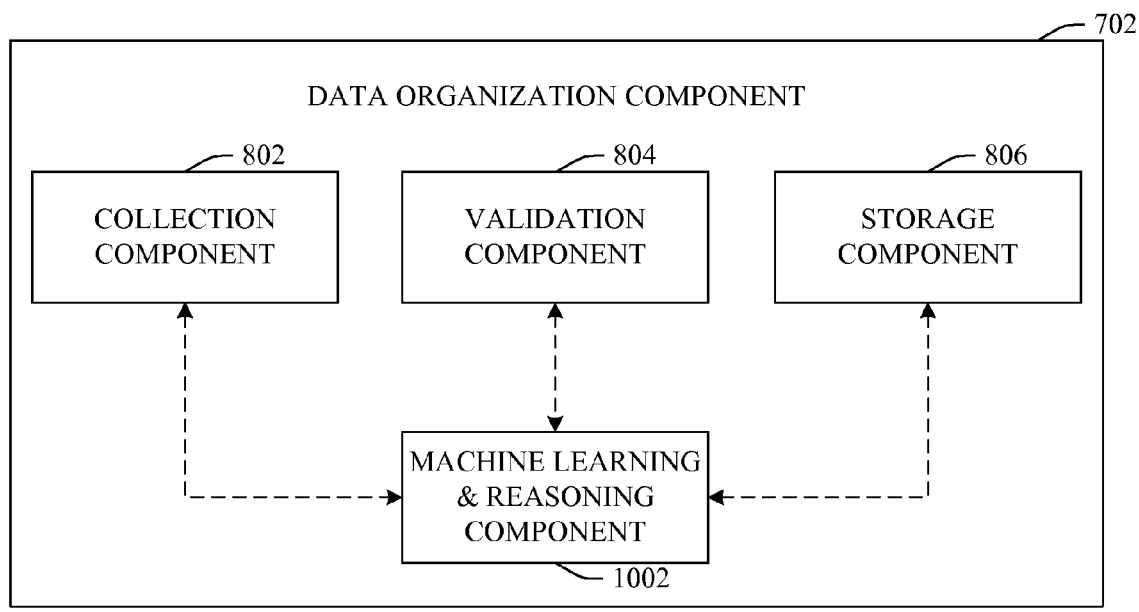
FIG. 10 illustrates an alternative block diagram of a data organization component that includes machine learning and reasoning (MLR) component that can automate functionality in accordance with an aspect of the innovation.

FIG. 10 illustrates an alternative block diagram of an example data organization component 702 that employs a machine learning and reasoning (MLR) component 1002 which facilitates automating one or more features in accordance with the subject innovation. The subject innovation (e.g., in connection with data atomization, threshold/policy generation, validation, analysis, clustering) can employ various MLR-based schemes for carrying out various aspects thereof. For example, a process for determining what criteria should be employed when determining the smallest meaningful bit of information can be facilitated via an automatic classifier system and process. Moreover, where the data network (e.g., 106 of FIG. 1) is distributed over various locations, the classifier can be employed to determine which location should be selected in order to effectively cluster and/or store data elements to optimize usability, traversal and/or mining operations.

A classifier is a function that maps an input attribute vector, $x=(x1, x2, x3, x4, xn)$, to a confidence that the input belongs to a class, that is, $f(x)=confidence(class)$. Such classification can employ a probabilistic and/or statistical-based analysis (e.g., factoring into the analysis utilities and costs) to prognose or infer an action that a user desires to be automatically performed.

A support vector machine (SVM) is an example of a classifier that can be employed. The SVM operates by finding a hypersurface in the space of possible inputs, which the hypersurface attempts to split the triggering criteria from the non-triggering events. Intuitively, this makes the classification correct for testing data that is near, but not identical to training data. Other directed and undirected model classification approaches include, e.g., naive Bayes, Bayesian networks, decision trees, neural networks, fuzzy logic models, and probabilistic classification models providing different patterns of independence can be employed. Classification as used herein also is inclusive of statistical regression that is utilized to develop models of priority.

As will be readily appreciated from the subject specification, the subject innovation can employ classifiers that are explicitly trained (e.g., via a generic training data) as well as implicitly trained (e.g., via observing user behavior, receiving extrinsic information). For example, SVM's are configured via a learning or training phase within a classifier constructor and feature selection module. Thus, the classifier(s) can be used to automatically learn and perform a number of functions, including but not limited to determining according to a predetermined criteria when to gather data, what granularity to use with regard to tagging, how to determine meaningful bits, where to store data elements to enhance usability, etc.

Figure 11:
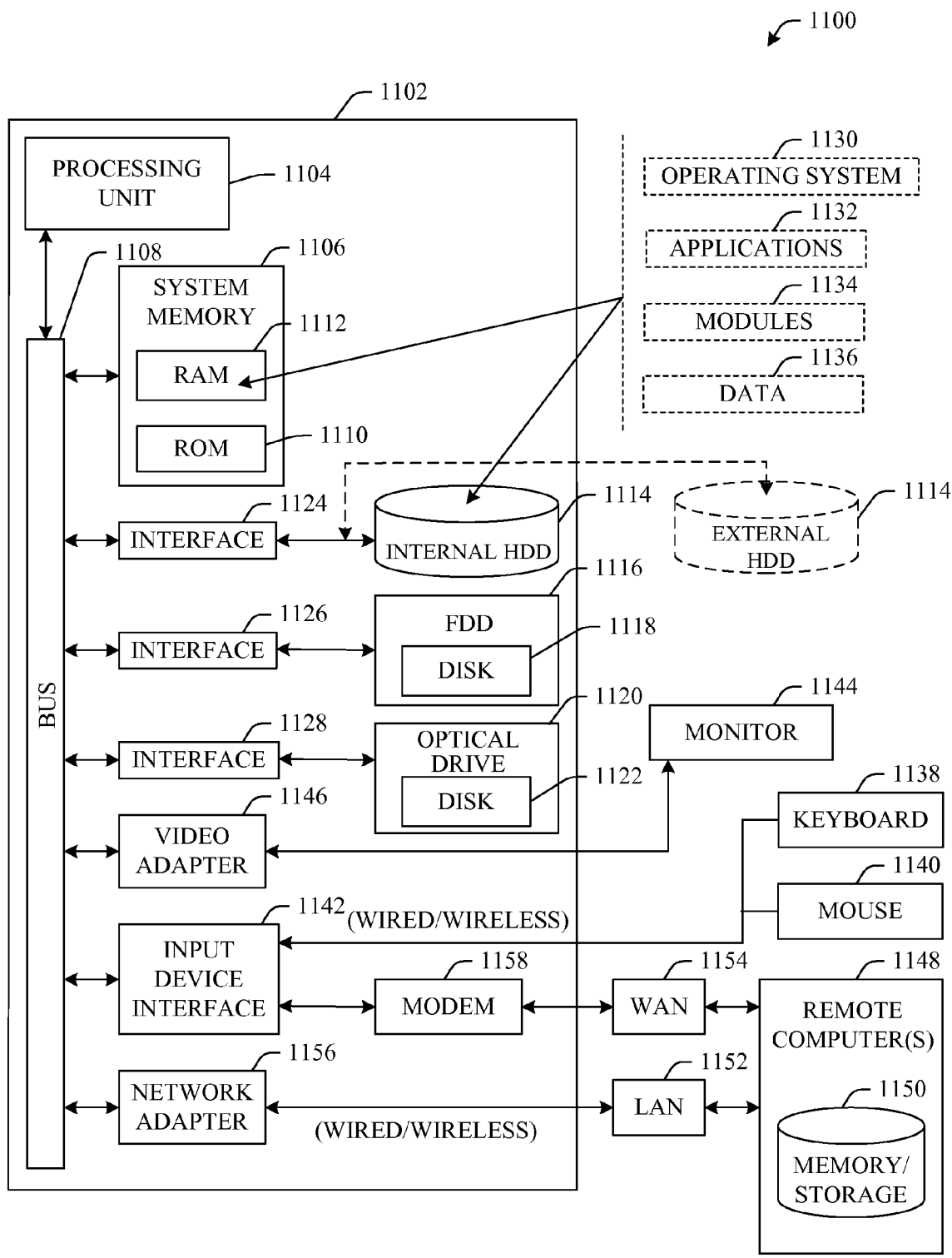
FIG. 11 illustrates a block diagram of a computer operable to execute the disclosed architecture.

Referring now to FIG. 11, there is illustrated a block diagram of a computer operable to execute the disclosed architecture. In order to provide additional context for various aspects of the subject innovation, FIG. 11 and the following discussion are intended to provide a brief, general description of a suitable computing environment 1100 in which the various aspects of the innovation can be implemented. While the innovation has been described above in the general context of computer-executable instructions that may run on one or more computers, those skilled in the art will recognize that the innovation also can be implemented in combination with other program modules and/or as a combination of hardware and software.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, as well as personal computers, hand-held computing devices, microprocessor-based or programmable consumer electronics, and the like, each of which can be operatively coupled to one or more associated devices.

The illustrated aspects of the innovation may also be practiced in distributed computing environments where certain tasks are performed by remote processing devices that are linked through a communications network. In a distributed computing environment, program modules can be located in both local and remote memory storage devices.

A computer typically includes a variety of computer-readable media. Computer-readable media can be any available media that can be accessed by the computer and includes both volatile and nonvolatile media, removable and non-removable media. By way of example, and not limitation, computer-readable media can comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disk (DVD) or other optical disk storage, magnetic cassettes, magnetic tape, magnetic disk storage or other magnetic storage devices, or any other medium which can be used to store the desired information and which can be accessed by the computer.

Communication media typically embodies computer-readable instructions, data structures, program modules or other data in a modulated data signal such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer-readable media.

With reference again to FIG. 11, the exemplary environment 1100 for implementing various aspects of the innovation includes a computer 1102, the computer 1102 including a processing unit 1104, a system memory 1106 and a system bus 1108. The system bus 1108 couples system components including, but not limited to, the system memory 1106 to the processing unit 1104. The processing unit 1104 can be any of various commercially available processors. Dual microprocessors and other multi-processor architectures may also be employed as the processing unit 1104.

The system bus 1108 can be any of several types of bus structure that may further interconnect to a memory bus (with or without a memory controller), a peripheral bus, and a local bus using any of a variety of commercially available bus architectures. The system memory 1106 includes read-only memory (ROM) 1110 and random access memory (RAM) 1112. A basic input/output system (BIOS) is stored in a non-volatile memory 1110 such as ROM, EPROM, EEPROM, which BIOS contains the basic routines that help to transfer information between elements within the computer 1102, such as during start-up. The RAM 1112 can also include a high-speed RAM such as static RAM for caching data.

The computer 1102 further includes an internal hard disk drive (HDD) 1114 (e.g., EIDE, SATA), which internal hard disk drive 1114 may also be configured for external use in a suitable chassis (not shown), a magnetic floppy disk drive (FDD) 1116, (e.g., to read from or write to a removable diskette 1118) and an optical disk drive 1120, (e.g., reading a CD-ROM disk 1122 or, to read from or write to other high capacity optical media such as the DVD). The hard disk drive 1114, magnetic disk drive 1116 and optical disk drive 1120 can be connected to the system bus 1108 by a hard disk drive interface 1124, a magnetic disk drive interface 1126 and an optical drive interface 1128, respectively. The interface 1124 for external drive implementations includes at least one or both of Universal Serial Bus (USB) and IEEE 1394 interface technologies. Other external drive connection technologies are within contemplation of the subject innovation.

The drives and their associated computer-readable media provide nonvolatile storage of data, data structures, computer-executable instructions, and so forth. For the computer 1102, the drives and media accommodate the storage of any data in a suitable digital format. Although the description of computer-readable media above refers to a HDD, a removable magnetic diskette, and a removable optical media such as a CD or DVD, it should be appreciated by those skilled in the art that other types of media which are readable by a computer, such as zip drives, magnetic cassettes, flash memory cards, cartridges, and the like, may also be used in the exemplary operating environment, and further, that any such media may contain computer-executable instructions for performing the methods of the innovation.

A number of program modules can be stored in the drives and RAM 1112, including an operating system 1130, one or more application programs 1132, other program modules 1134 and program data 1136. All or portions of the operating system, applications, modules, and/or data can also be cached in the RAM 1112. It is appreciated that the innovation can be implemented with various commercially available operating systems or combinations of operating systems.

A user can enter commands and information into the computer 1102 through one or more wired/wireless input devices, e.g., a keyboard 1138 and a pointing device, such as a mouse 1140. Other input devices (not shown) may include a microphone, an IR remote control, a joystick, a game pad, a stylus pen, touch screen, or the like. These and other input devices are often connected to the processing unit 1104 through an input device interface 1142 that is coupled to the system bus 1108, but can be connected by other interfaces, such as a parallel port, an IEEE 1394 serial port, a game port, a USB port, an IR interface, etc.

A monitor 1144 or other type of display device is also connected to the system bus 1108 via an interface, such as a video adapter 1146. In addition to the monitor 1144, a computer typically includes other peripheral output devices (not shown), such as speakers, printers, etc.

The computer 1102 may operate in a networked environment using logical connections via wired and/or wireless communications to one or more remote computers, such as a remote computer(s) 1148. The remote computer(s) 1148 can be a workstation, a server computer, a router, a personal computer, portable computer, microprocessor-based entertainment appliance, a peer device or other common network node, and typically includes many or all of the elements described relative to the computer 1102, although, for purposes of brevity, only a memory/storage device 1150 is illustrated. The logical connections depicted include wired/wireless connectivity to a local area network (LAN) 1152 and/or larger networks, e.g. a wide area network (WAN) 1154. Such LAN and WAN networking environments are commonplace in offices and companies, and facilitate enterprise-wide computer networks, such as intranets, all of which may connect to a global communications network, e.g., the Internet.

When used in a LAN networking environment, the computer 1102 is connected to the local network 1152 through a wired and/or wireless communication network interface or adapter 1156. The adapter 1156 may facilitate wired or wireless communication to the LAN 1152, which may also include a wireless access point disposed thereon for communicating with the wireless adapter 1156.

When used in a WAN networking environment, the computer 1102 can include a modem 1158, or is connected to a communications server on the WAN 1154, or has other means for establishing communications over the WAN 1154, such as by way of the Internet. The modem 1158, which can be internal or external and a wired or wireless device, is connected to the system bus 1108 via the serial port interface 1142. In a networked environment, program modules depicted relative to the computer 1102, or portions thereof, can be stored in the remote memory/storage device 1150. It will be appreciated that the network connections shown are exemplary and other means of establishing a communications link between the computers can be used.

The computer 1102 is operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, restroom), and telephone. This includes at least Wi-Fi and Bluetooth™ wireless technologies. Thus, the communication can be a predefined structure as with a conventional network or simply an ad hoc communication between at least two devices.

Wi-Fi, or Wireless Fidelity, allows connection to the Internet from a couch at home, a bed in a hotel room, or a conference room at work, without wires. Wi-Fi is a wireless technology similar to that used in a cell phone that enables such devices, e.g., computers, to send and receive data indoors and out; anywhere within the range of a base station. Wi-Fi networks use radio technologies called IEEE 802.11 (a, b, g, etc.) to provide secure, reliable, fast wireless connectivity. A Wi-Fi network can be used to connect computers to each other, to the Internet, and to wired networks (which use IEEE 802.3 or Ethernet). Wi-Fi networks operate in the unlicensed 2.4 and 5 GHz radio bands, at an 11 Mbps (802.11a) or 54 Mbps (802.11b) data rate, for example, or with products that contain both bands (dual band), so the networks can provide real-world performance similar to the basic 10 BaseT wired Ethernet networks used in many offices.

Figure 12:
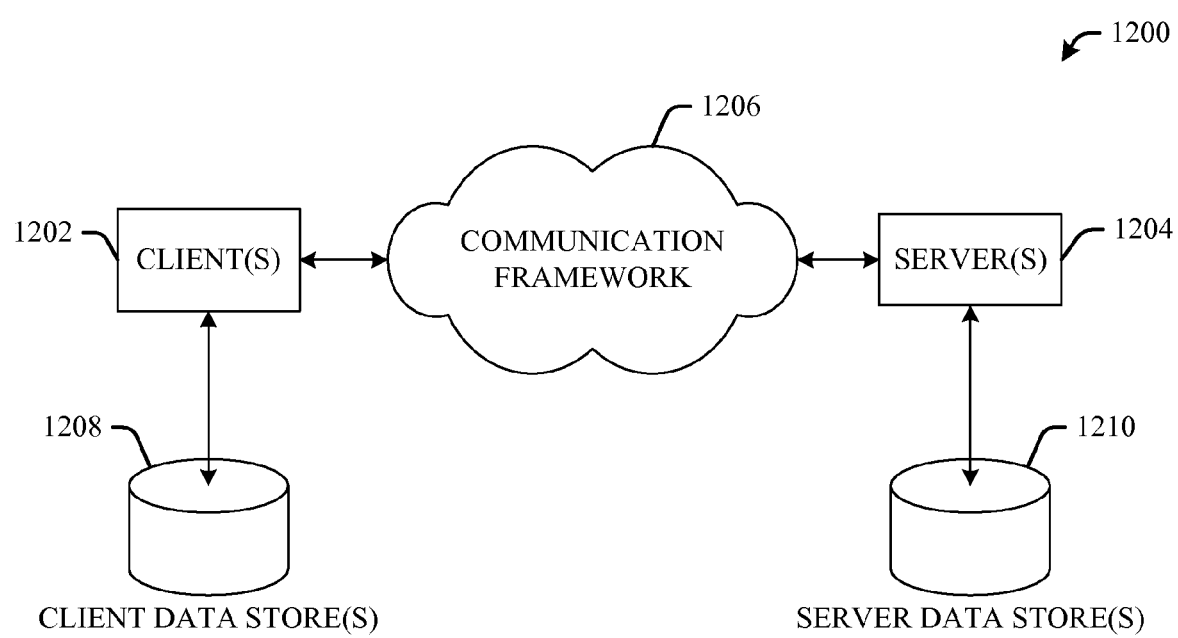
FIG. 12 illustrates a schematic block diagram of an exemplary computing environment in accordance with the subject innovation.

Referring now to FIG. 12, there is illustrated a schematic block diagram of an exemplary computing environment 1200 in accordance with the subject innovation. The system 1200 includes one or more client(s) 1202. The client(s) 1202 can be hardware and/or software (e.g., threads, processes, computing devices). The client(s) 1202 can house cookie(s) and/or associated contextual information by employing the innovation, for example.

The system 1200 also includes one or more server(s) 1204. The server(s) 1204 can also be hardware and/or software (e.g., threads, processes, computing devices). The servers 1204 can house threads to perform transformations by employing the innovation, for example. One possible communication between a client 1202 and a server 1204 can be in the form of a data packet adapted to be transmitted between two or more computer processes. The data packet may include a cookie and/or associated contextual information, for example. The system 1200 includes a communication framework 1206 (e.g., a global communication network such as the Internet) that can be employed to facilitate communications between the client(s) 1202 and the server(s) 1204.

Communications can be facilitated via a wired (including optical fiber) and/or wireless technology. The client(s) 1202 are operatively connected to one or more client data store(s) 1208 that can be employed to store information local to the client(s) 1202 (e.g., cookie(s) and/or associated contextual information). Similarly, the server(s) 1204 are operatively connected to one or more server data store(s) 1210 that can be employed to store information local to the servers 1204.

What has been described above includes examples of the innovation. It is, of course, not possible to describe every conceivable combination of components or methodologies for purposes of describing the subject innovation, but one of ordinary skill in the art may recognize that many further combinations and permutations of the innovation are possible. Accordingly, the innovation is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A computer-implemented system comprising:
 a processor configured to execute computer-executable components; and
 memory storing computer-executable components for establishing a self-describing data network configured with a plurality of self-describing health-related data elements, the computer-executable components including:
  an interface layer component configured to provide a gateway between sources of health-related data elements and the self-describing data network;
  a data atomizing component configured to generate self-describing health-related data elements based on health-related data elements received from the sources by:

determining granularity to use with regard to tagging the health-related data elements received from the sources, wherein the health-related data elements include a health-related data element representing a measurement of a patient;

de-constructing the health-related data element representing the measurement of the patient until a core data item portion representing a smallest meaningful element is determined, wherein: the core data item portion includes only a value of the measurement, the health-related data element is de-constructed into the core data item portion and a metadata portion that includes descriptive attributes about the core data item portion, and the metadata portion identifies an origin of the measurement, a measurement type, the patient, and a healthcare professional that administered the measurement; and wrapping the core data item portion with a plurality of tags representing the descriptive attributes to a generate a self-describing health-related data element, wherein the tags are configured to establish relationships between the self-describing health-related data element and other self-describing health-related data elements of the self-describing data network;

an accuracy validation component configured to validate accuracy of the value of the measurement included in the core data item portion based on the measurement type, the patient, and the healthcare professional identified in the tags wrapping the core data item portion prior to adding the self-describing health-related data element to the self-describing data network;

an origin validation component configured to authenticate the source of the health-related data element based on the origin identified in the tags wrapping the core data item portion prior to adding the self-describing health-related data element to the self-describing data network; and a storage component configured to employ the tags wrapping the core data item portion to interrelate the self-describing health-related data element to other self-describing health-related data elements included in the self-describing data network.

2. The computer-implemented system of claim 1, wherein the computer-executable components further comprise:
a collection component configured to automatically collect health-related data elements.

3. The computer-implemented system of claim 2, wherein the health-related data elements are collected from users of the self-describing data network.

4. The computer-implemented system of claim 2, wherein the collection component is configured to monitor physiological sensors.

5. The computer-implemented system of claim 1, wherein the computer-executable components further comprise:
an attribute collection component configured to gather additional descriptive metadata to incorporate into the self-describing health-related data element.

6. The computer-implemented system of claim 5, wherein the additional descriptive metadata is based, at least, in part, on relationships to other medical records.

7. The computer-implemented system of claim 1, wherein the accuracy validation component is configured to confirm that the value of the measurement falls within a range of values for the measurement.

8. The computer-implemented system of claim 1, wherein the accuracy validation component is configured to validate the accuracy of the value of the measurement based on similarity of the value of the measurement to previous measurements of the patient, experience of the health care professional that administered the measurement, and an age of a measuring device that was used to take the measurement.

9. The computer-implemented system of claim 1, wherein the computer-executable components further comprise:
a relationship analysis component configured to identify relationships between a subset of self-describing health-related data elements on an as-needed, just-in-time basis.

10. The computer-implemented system of claim 9, wherein the computer-executable components further comprise:
a location determining component configured to cluster the self-describing health-related data elements of the subset based, at least, in part, on an analysis performed by the relationship analysis component.

11. The computer-implemented system of claim 1, wherein the source of the health-related data element is an application.

12. The computer-implemented system of claim 1, wherein the computer-executable component further comprise:
a machine learning and reasoning component configured to employ at least one of a probabilistic-based analysis or a statistical-based analysis to determine criteria for de-constructing health-related data elements.

13. A computer-implemented method of establishing a self-describing data network configured with a plurality of self-describing health-related data elements, the computer-implemented method comprising:
providing a gateway between sources of health-related data elements and the self-describing data network;
generating self-describing health-related data elements based on health-related data elements received from the sources by:
determining granularity to use with regard to tagging the health-related data elements received from the sources, wherein the health-related data elements include a health-related data element representing a measurement of a patient;
de-constructing the health-related data element representing the measurement of the patient until a core data item portion representing a smallest meaningful element is determined, wherein: the core data item portion includes only a value of the measurement, the health-related data element is de-constructed into the core data item portion and a metadata portion that includes descriptive attributes about the core data item portion, and the metadata portion identifies an origin of the measurement, a measurement type, the patient, and a healthcare professional that administered the measurement; and
wrapping the core data item portion with a plurality of tags representing the descriptive attributes to a generate a self-describing health-related data element, wherein the tags are configured to establish relationships between the self-describing health-related data element and other self-describing health-related data elements of the self-describing data network;
validating accuracy of the value of the measurement included in the core data item portion based on the measurement type, the patient, and the healthcare professional identified in the tags wrapping the core data item portion prior to adding the self-describing health-related data element to the self-describing data network;

authenticating the source of the health-related data element based on the origin identified in the tags wrapping the core data item portion prior to adding the self-describing health-related data element to the self-describing data network; and employing the tags wrapping the core data item portion to interrelate the self-describing health-related data element to other self-describing health-related data elements included in the self-describing data network.

14. The computer-implemented method of claim 13, further comprising verifying that the value of the measurement falls within a range of values for the measurement.

15. The computer-implemented method of claim 13, further comprising:
    collecting additional descriptive metadata based on relationships to other medical records; and
    tagging the core data portion with the additional descriptive metadata.

16. The computer-implemented method of claim 13, further comprising:
    identifying relationships between a subset of self-describing health-related data elements; and
    clustering the self-describing health-related data elements of the subset based at least, in part, on the relationships.

17. A computer-readable storage device storing computer-executable instructions for establishing a self-describing data network configured with a plurality of self-describing health-related data elements, the computer-executable instructions comprising instructions for:
    providing a gateway between sources of health-related data elements and the self-describing data network;
    generating self-describing health-related data elements based on health-related data elements received from the sources by:
        determining granularity to use with regard to tagging the health-related data elements received from the sources, wherein the health-related data elements include a health-related data element representing a measurement of a patient;
        de-constructing the health-related data element representing the measurement of the patient until a core data item portion representing a smallest meaningful element is determined, wherein: the core data item portion includes only a value of the measurement, the health-related data element is de-constructed into the core data item portion and a metadata portion that includes descriptive attributes about the core data item portion, and the metadata portion identifies an origin of the measurement, a measurement type, the patient, and a healthcare professional that administered the measurement; and
        wrapping the core data item portion with a plurality of tags representing the descriptive attributes to a generate a self-describing health-related data element, wherein the tags are configured to establish relationships between the self-describing health-related data element and other self-describing health-related data elements of the self-describing data network;
    validating accuracy of the value of the measurement included in the core data item portion based on the measurement type, the patient, and the healthcare professional identified in the tags wrapping the core data item portion prior to adding the self-describing health-related data element to the self-describing data network;
    authenticating the source of the health-related data element based on the origin identified in the tags wrapping the core data item portion prior to adding the self-describing health-related data element to the self-describing data network; and
    employing the tags wrapping the core data item portion to interrelate the self-describing health-related data element to other self-describing health-related data elements included in the self-describing data network.

18. The computer-readable storage device of claim 17, wherein the computer-executable instructions further comprise instructions for:
    collecting additional descriptive metadata based on relationships to other medical records; and
    tagging the core data portion with the additional descriptive metadata.

19. The computer-readable storage device of claim 17, wherein the computer-executable instructions further comprise instructions for:
    verifying that the value of the measurement falls within a range of values for the measurement.

20. The computer-readable storage device of claim 17, wherein the accuracy of the value of the measurement is validated based on similarity of the value of the measurement to previous measurements of the patient, experience of the health care professional that administered the measurement, and an age of a measuring device that was used to take the measurement.

* * * * *